US00PP26185P3

(12) United States Plant Patent
Lintott et al.

(10) Patent No.: US PP26,185 P3
(45) Date of Patent: Dec. 1, 2015

(54) ***LEUCANTHEMUM* PLANT NAMED 'REAL NEAT'**

(50) Latin Name: *Leucanthemum superbum*
Varietal Denomination: Real Neat

(71) Applicants: Keith George Lintott, Bognor Regis (GB); Charles Richard Read, Bognor Regis (GB)

(72) Inventors: Keith George Lintott, Bognor Regis (GB); Charles Richard Read, Bognor Regis (GB)

( * ) Notice: Subject to any disclaimer, the term of this patent is extended or adjusted under 35 U.S.C. 154(b) by 92 days.

(21) Appl. No.: 13/999,841

(22) Filed: Mar. 27, 2014

(65) Prior Publication Data

US 2014/0310841 P1 Oct. 16, 2014

Related U.S. Application Data

(60) Provisional application No. 61/853,747, filed on Apr. 11, 2013.

(51) Int. Cl.
*A01H 5/02* (2006.01)

(52) U.S. Cl.
USPC ..... Plt./285
CPC ..... *A01H 5/025* (2013.01)

(58) Field of Classification Search
USPC ..... Plt./285
See application file for complete search history.

*Primary Examiner* — Susan McCormick Ewoldt
(74) *Attorney, Agent, or Firm* — Barbara Campbell; Cochran Freund & Young LLC

(57) ABSTRACT

A new cultivar of *Leucanthemum* plant named 'Real Neat' that is distinguishable by a tight clumping habit, dark green foliage and inflorescences comprised of many pure white ray florets, tubular in shape becoming flared at the apex, arranged in two layers surrounding a golden yellow central disc and carried on strong stems, is disclosed.

2 Drawing Sheets

Genus and species: *Leucanthemum superbum.*
Variety denomination: 'Real Neat'.

BACKGROUND OF THE NEW PLANT

The present invention relates to a new and distinct cultivar of *Leucanthemum* commonly known as Shasta daisy, which is grown as an ornamental plant for use in the garden and landscape. The new cultivar is known botanically as *Leucanthemum superbum* and will be referred to hereinafter by the cultivar name 'Real Neat'.

*Leucanthemum* is a genus within the family Asteraceae in which the commonly referred to "flower" is botanically the inflorescence which is comprised of outer showy ray florets surrounding smaller disc florets.

'Real Neat' arose and was selected from an ongoing breeding program which is conducted in West Sussex, United Kingdom. The breeding program commenced in 2006 with the aim of developing new and improved commercial varieties of *Leucanthemum*. Each year's breeding cycle consists of controlled pollination between chosen male and female parents including unnamed and unreleased seedlings retained from previous breeding cycles. Seed from each year's cycle is harvested and sown in early February of the following year after harvest, and new seedlings are raised and evaluated in the following summer.

'Real Neat' is a seedling selection that resulted from the controlled pollination of a single plant of *Leucanthemum* code number 'L701-1' (unreleased seedling retained from a previous breeding generation) as the female parent, using pollen from a single plant of *Leucanthemum* 'Real Joy' (L35) (unreleased, unpatented) as the male parent. 'Real Neat' was selected based on the criteria of vigor, formal pure white flowers and strong stiff stems.

'Real Neat' was first asexually propagated in West Sussex, United Kingdom in 2008 using the method of vegetative division and subsequently by basal shoot cuttings. Since that time under careful observation, the distinguishing characteristics of 'Real Neat' have been determined to be uniform, stable and true to type in subsequent generations of asexual propagation via vegetative division and subsequently by basal shoot cuttings.

SUMMARY

The following traits have been repeatedly observed and represent the distinguishing characteristics of 'Real Neat'. 'Real Neat' has not been tested under all possible conditions and phenotypic differences may be observed with variations in environmental, climatic, and cultural conditions, however, without any variance in genotype.

1. 'Real Neat' exhibits tight clumping habit.
2. The foliage of 'Real Neat' is dark green in color.
3. The inflorescence of 'Real Neat' is 6 cm in diameter and comprised of ray florets arranged around the central disc.
4. The ray florets of 'Real Neat' are tubular in shape becoming flared at the apex.
5. The ray florets of 'Real Neat' are pure white in color.
6. The ray florets of 'Real Neat' are arranged in two layers around a deep golden yellow central disc.
7. The inflorescence of 'Real Neat' is carried on a strong stiff stem.
8. Flowering of 'Real Neat' commences in early summer and continues until fall.
9. After one year of growth in a 1 gallon container, a plant of 'Real Neat' is 40 cm in height and 35 cm in width.
10. 'Real Neat' prefers a rich moist well-drained medium.

11. 'Real Neat' is hardy in USDA Zone 5 (−20° F. or −28° C.).

DESCRIPTION OF THE PHOTOGRAPHS

The accompanying color photographs illustrate the overall appearance of the new *Leucanthemum* cultivar named 'Real Neat' showing the color of foliage and flower as true as is reasonably possible to obtain in color reproductions of this type. Color in the photographs may differ from color values cited in the detailed botanical description, which accurately describe the actual color of 'Real Neat'. Both photographs were made using conventional techniques and although flower and foliage color may appear different from actual color due to light reflectance, it is as accurate as possible by conventional photography.

DESCRIPTION OF THE NEW VARIETY

Figure 1:
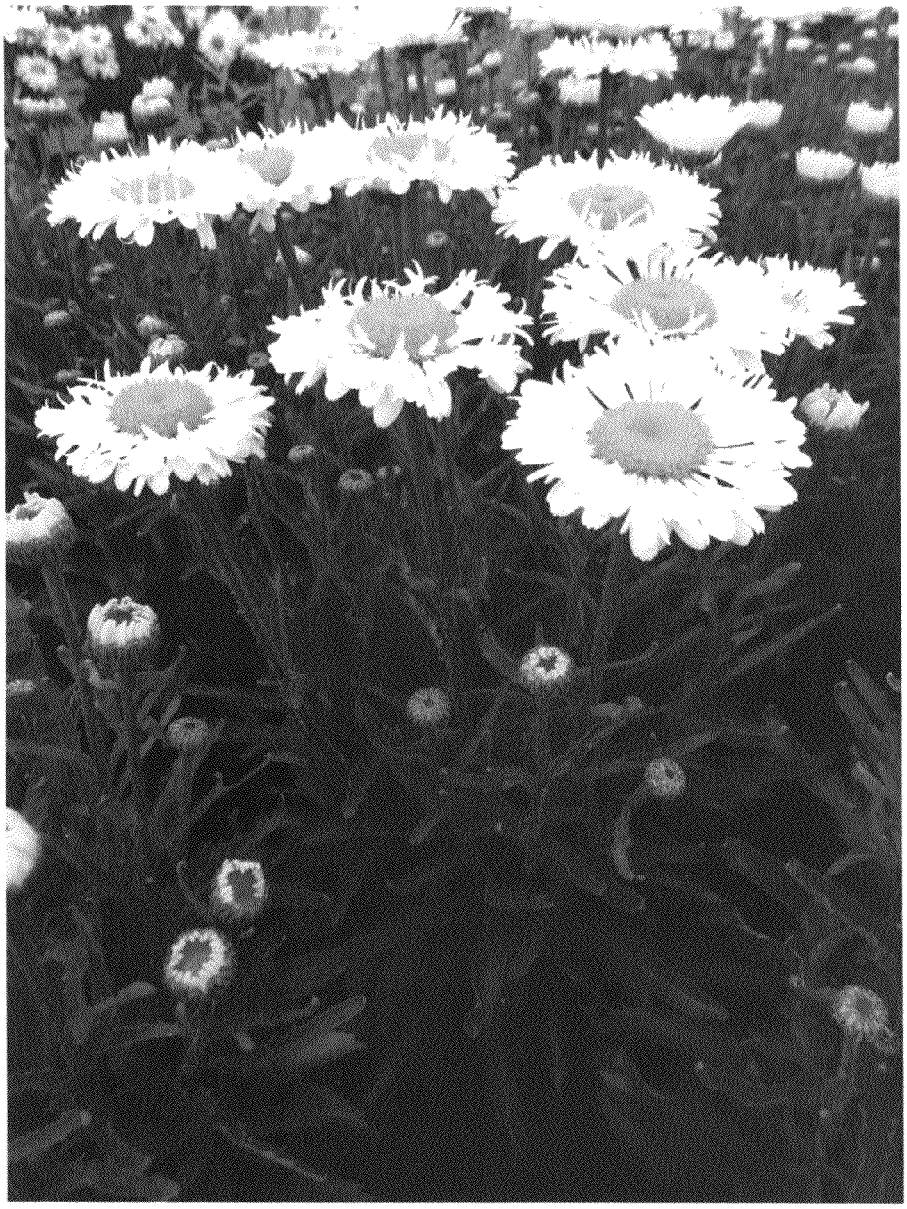
FIG. 1 illustrates in the foreground a nine months old plant (from initial cuttings) growing in a 2-liter container outdoors in West Sussex, United Kingdom. The illustrated plants have not been pinched or treated with any chemical growth regulators.
Figure 2:
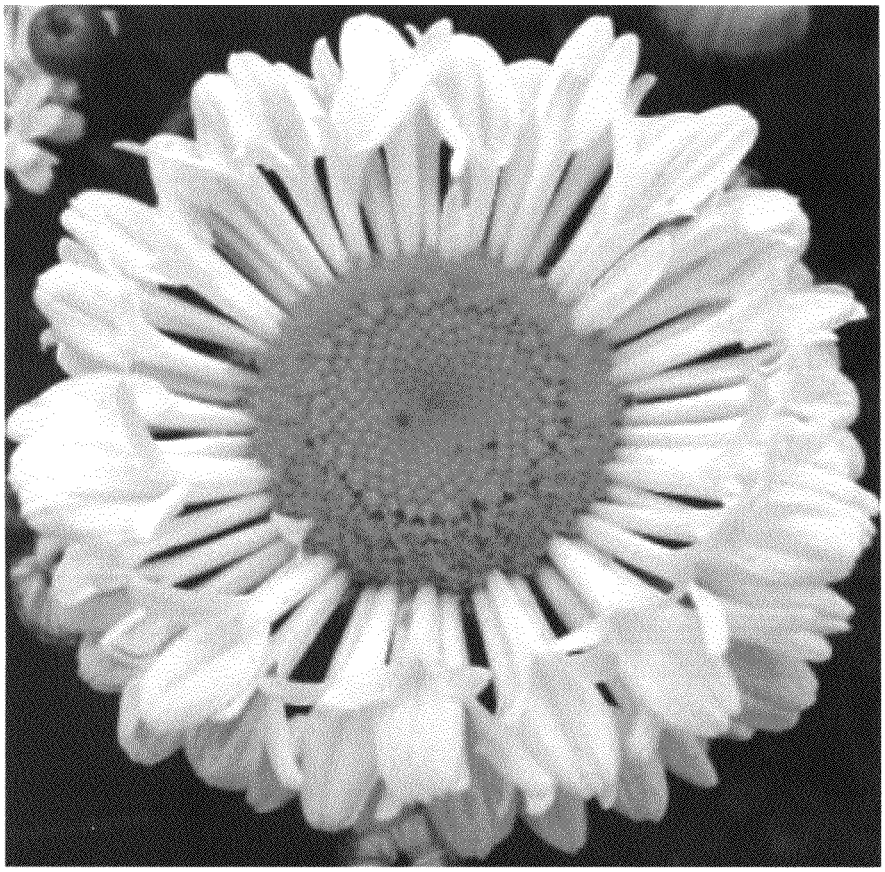
FIG. 2 depicts a close-up view of the inflorescence of a plant of 'Real Neat'.

The following is a detailed botanical description of the new cultivar 'Real Neat'. Observations, measurements, values and comparisons were collected in Santa Barbara, Calif. from a 12 month-old plant growing outdoors in the garden border. Color determinations are made in accordance with The 2007 Royal Horticultural Society Colour Chart from London, England, except where general color terms of ordinary dictionary significance are used.

Classification:

*Genus and species.*—*Leucanthemum superbum.*
*Denomination.*—'Real Neat'.
*Common name.*—Shasta daisy.

Parentage:

*Female parent.*—*Leucanthemum* plant 'L701-1' unreleased proprietary seedling, unpatented).
*Male parent.*—*Leucanthemum* plant 'Real Joy' (or also known as 'L35', unreleased, unpatented).

Plant:

*Habit.*—Tight clumping habit.
*Commercial category.*—Perennial herb.
*Use.*—For garden and landscape.
*Suggested commercial container size.*—4-inch and 1-liter containers.
*Propagation method.*—Basal shoot cuttings and division.
*Rooting system.*—Fine and fibrous.
*Vigor.*—Vigorous.
*Time to develop roots* (*range*).—14 to 20 days are needed for an initial cutting to develop roots.
*Temperature to develop roots* (*range*).—The recommended air temperature is 20-21° Centigrade.
*Crop time* (*range*).—4 to 6 months to produce a 1-liter container from a basal shoot cutting.
*Plant dimensions* (*one year*).—40 cm in height and 35 cm in width.
*Cultural requirements.*—Grow in full sun and rich, moist moderately fertile well-draining soil.
*Hardiness.*—USDA Zone 5.

Stems:

*Branching.*—Basal.
*Color.*—146A.
*Basal stem length.*—15 cm.
*Diameter.*—6 mm to 1 cm.
*Shape.*—Cylindrical.
*Surface.*—Furrowed, farinaceous.

Foliage:

*Type.*—Evergreen.
*Arrangement* (*combination*).—Opposite and basal.
*Internode length* (*range*).—0.5 cm to 1.0 cm.
*Division.*—Simple.
*Margin.*—Serrate; teeth spaced at 4 mm to 6 mm intervals, depth 2 mm.
*Apex.*—Acute.
*Base.*—Attenuate.
*Leaf attachment* (*range*).—Basal to sessile.
*Leaf color* (*abaxial surface*).—N137B.
*Leaf color* (*adaxial surface*).—137D.
*Leaf shape.*—Lanceolate.
*Leaf dimensions* (*when fully expanded*).—20 cm in length, 3 cm in width.
*Leaf venation.*—Pinnate.
*Vein color* (*both surfaces*).—145A.
*Leaf surface* (*both surfaces*).—Glabrous.

Inflorescence:

*Inflorescence type.*—Capitulum.
*Inflorescence quantity* (*average*).—30 (including buds) per 2-liter container plant.
*Inflorescence diameter.*—6 cm.
*Inflorescence depth.*—3.5 cm.
*Inflorescence shape.*—Radiate; ray florets densely arranged around receptacle, mostly in two layers.
*Inflorescence color.*—Central disc color: Ranges between 23A and N163D. Ray floret color: Pure bright white, nearest to NN155D.
*Fragrance.*—Light sweetly perfumed.
*Aspect.*—Disc facing upward.
*Bud dimensions.*—0.50 cm in height and 1.0 cm in diameter.
*Bud shape.*—Flattened sphere.
*Bud color.*—147B.
*Bud surface.*—Glabrous.
*Blooming season.*—Early summer to fall.
*Peduncle shape.*—Cylindrical.
*Peduncle length.*—14 cm to 20 cm.
*Peduncle diameter.*—4 mm to 5 mm.
*Peduncle surface.*—Furrowed with sparse hairs.
*Peduncle color.*—144A.
*Ray florets.*—Ray floret shape: Tubular, quilled. Ray floret quantity: 60 to 70 per inflorescence. Ray floret arrangement: Radiate. Ray floret corolla tube dimensions: 6 mm to 8 mm in length, 1.5 mm in diameter. Ray floret corolla tube color: Pure bright white, nearest to NN155D. Petal shape: Elliptic, lightly ribbed. Petal surface (abaxial): Glabrous. Petal surface (adaxial): Pubescent. Petal apex: Rounded, emarginate. Petal margin: Entire. Petal dimensions: 8 mm in length and 4 mm to 5 mm in width. Petal color: Pure bright white, nearest to NN155D.
*Disc floret.*—Disc diameter: 3 cm. Disc floret quantity: Numerous, approximately 400 to 500 per inflorescence, massed at center of receptacle. Disc floret color: Ranges between 23A and N163D. Disc floret dimensions: 4 mm in depth and 1 mm in diameter. Disc floret shape: Tubular, rarely opens. Disc floret petals: Ranges from 3 to 5 in number, basally fused.

Disc floret petal color: Ranges between 23A and N163D. Disc floret petal apex: Acute.

*Receptacle color.*—147B.

*Receptacle shape*.—Convex.

*Receptacle dimensions.*—0.5 cm in height and 2.5 cm in diameter.

*Lastingness of inflorescence* (*range*).—10 to 12 days on the plant; ray florets are persistent.

Seed: Not observed to date.

Disease and pest resistance/susceptibility: No disease or pest resistance known to the inventors.

COMPARISON WITH PARENTAL LINES AND KNOWN VARIETY

'Real Neat' is distinguishable from the female parent, 'L701-1' by vigor. 'Real Neat' exhibits considerably more vigor than 'L701-1'. 'Real Neat' is distinguishable from the male parent, 'Real Joy' by its tubular shaped petals. Whereas 'Real Joy' exhibits white flowers with mostly flat petals slightly cupped where attached to the central disk, 'Real Neat' exhibits white flowers with tubular petals.

The closest variety in overall appearance to 'Real Neat' can be considered to be *Leucanthemum* 'Becky' (unpatented). Whereas the inflorescence of 'Real Neat' is comprised of two layers of ray florets, the ray florets of 'Becky' are arranged in a single layer. In addition, the ray florets of 'Real Neat' are tubular in shape, while 'Becky' exhibits flat ray florets.

We claim:

1. A new and distinct variety of *Leucanthemum* plant named 'Real Neat' as shown and described herein.

* * * * *